United States Patent [19]
Siddiqui et al.

[11] Patent Number: 6,120,758
[45] Date of Patent: Sep. 19, 2000

[54] PRESERVATIVE SYSTEM FOR TOPICALLY APPLIED PRODUCTS

[75] Inventors: Mukhtar Siddiqui, San Ramon; Ener H. Flores; Evangeline R. Basa, both of Hayward, all of Calif.

[73] Assignee: Shaklee Corporation, Pleasonton, Calif.

[21] Appl. No.: 09/118,312

[22] Filed: Jul. 16, 1998

[51] Int. Cl.$^7$ ..................................................... A61K 31/74
[52] U.S. Cl. ...................... 424/78.02; 424/401; 424/404; 514/844; 514/887; 514/938
[58] Field of Search ................................. 424/78.02, 401, 424/404, 78.03, 78.07; 514/886, 887, 844, 938

[56] References Cited

U.S. PATENT DOCUMENTS 5,683,683 11/1997 Scafidi .................................. 424/70.19

*Primary Examiner*—S. Mark Clardy
*Assistant Examiner*—Michael A. Williamson
*Attorney, Agent, or Firm*—Klarquist Sparkman Campbell Leigh & Whinston, LLP

[57] ABSTRACT

A preservative system for topically applied products includes one or more of benzyl alcohol, disodium EDTA, and a para-hydrobenzoic acid, in an effective antimicrobial amount, combined with one or more enhancers selected from the group of sorbic acid, salts of sorbic acid, benzoic acid, salts of benzoic acid, and a phospholipid. This preservative system has been found to effectively prevent the growth of bacteria, yeast and mold, without irritation of the skin as occurs with many prior preservatives. The preservative system is therefore ideal for incorporation into topical preparations such as cosmetics, skin care products, and pharmaceutical compositions (such as dermatologic, otic and ophthalmic preparations).

16 Claims, No Drawings

PRESERVATIVE SYSTEM FOR TOPICALLY APPLIED PRODUCTS

FIELD OF THE INVENTION

This invention relates to a preservative for topical compositions, particularly compositions that do not irritate the skin.

BACKGROUND OF THE INVENTION

Topically applied products, regardless of their use, usually contain water as one of the primary components. This water provides a medium in which microorganisms can survive or grow. Other ingredients in these formulations can also create a viable growth medium for these organisms, hence such formulations usually contain a preservative system. Preservative systems can be either a single agent or a combination of agents.

An ideal preservative system has a broad-spectrum of activity against all types of microorganisms, including yeast and mold, and gram-positive and gram-negative bacteria. The preservative is also ideally effective at low concentrations, to minimize expense and avoid irritation and/or sensitization reactions. The preservative should also be somewhat soluble in an aqueous portion of the formulation, but may also possess a limited solubility in an oleaginous portion of the formulation. Since microorganisms grow in water but fail to grow in media where water is absent, the preservative should be present in that portion of the product where it can be effectively assimilated by the microorganisms.

The preservative should also be compatible with the other ingredients in the formulation, and not react with or otherwise be inactivated by those ingredients. The preservative is ideally colorless and odorless, and remains so throughout the intended shelf-life of the product. It should also be stable throughout the expected life of the product, because many microorganisms can lay dormant in the composition until conditions are later appropriate for growth. If a preservative was unstable and degraded over the shelf-life of the product, contamination could occur once the preservative concentration fell below the threshold necessary to inhibit the growth of the microorganisms. Furthermore, the preservative is ideally stable to any changes in temperature and/or pH encountered during the manufacturing and packaging process, as well as the storage conditions encountered both prior to and after sale to the end user.

The preservative should also be safe, without exerting undesired biological effects on human skin cells. Even at typical use concentrations, many preservatives have the capacity to cause irritation and/or sensitization when in contact with human skin. Furthermore, since the concentrated preservative agents must be handled and incorporated into the product during the manufacturing process, these materials must not present an insurmountable hazard to the production workers making the product.

It is also helpful if the efficacy of the preservative can be assessed by an assay. Although preservative agents can be evaluated by conducting conventional preservative efficacy tests, such testing is slow and worker intensive. Therefore, it is often important to have a agent whose activity can be correlated to more conventional analytical methods for preservatives. Given the complexity of topical formulations and their respective preservative agents, it is unusual for a correlated analytical method to exist. Additionally, the preservative agents must be analyzable in order to ensure the quality of the material as it is received from the manufacturer.

The individual preservative agents are preferably easy to handle in their bulk state, prior to incorporation into a topical formulation, and inexpensive to use. More expensive preservatives are ideally effective at low concentrations to keep costs low.

No single preservative agent fulfills all of these criteria, and the requirements become even more complex when regulatory requirements are added to the criteria. Formulation scientists working in collaboration with microbiologists and analytical chemists expend a significant amount of effort in developing adequate preservative systems for topically applied products in an attempt to satisfy both practical and regulatory requirements.

Emulsion systems [for example, oil-in-water (o/w), water-in-oil (w/o), multiple emulsions including water-in-oil-in-water (w/o/w) and oil-in-water-in-oil (o/w/o) systems], liposomal systems and aqueous-based liquid, gel or suspension systems are the major product forms used for topical delivery systems in cosmetic, skincare, personal care, OTC pharmaceutical, ophthalmic, otic, dermatological and other prescription pharmaceutical products. All of these topical delivery systems contain water, as well as ingredients that support and/or sustain the growth of microorganisms such as bacteria, yeast and molds. Theses products therefore contain preservatives to kill or at least inhibit the growth of microorganisms, usually in low amounts to avoid affecting human skin cells to which they are applied. Government regulatory agencies also may regulate the concentrations of preservatives used, to protect the consumer by reducing the potential for irritation and/or allergic sensitization from topical application.

Some of the more commonly used preservatives in topically applied products include the following materials listed according to their International Nomenclature for Cosmetic Ingredients (INCI) name:

| | |
|---|---|
| Benzoic Acid (and salts) | Benzyl Alcohol |
| 2-bromo-2-nitropropane-1,3-diol | Chlorhexidine |
| Chloroxylenol | Dehydroacetic Acid (and salts) |
| Diazolidinyl Urea | DMDM Hydantion |
| Ethyl Alcohol | Imidazolidinyl Urea |
| Isothazolinones | Paraben Esters |
| Phenethyl Alcohol | Phenoxyethanol |
| Quaternim-15 | Sorbic Acid (and salts) |

The esters of p-hydrobenzoic acid are known as parabens, and include methyl, ethyl, propyl and butyl esters. Higher esters are even more active then the butyl esters, but decreasing solubility makes them less desirable to use. Alcohols that have been used as preservatives include ethyl and isopropyl alcohol, but benzyl and phenylethyl alcohol may also be used. Benzoic acid may be used either as the acid, or as a salt such as sodium benzoate.

Many of the topically applied products use either imidazolidinyl urea (Germall 115® from Sutton Labs) or diazolidinyl urea (Germall II® from Sutton Labs), in combination with parabens. However the inventors have found that this commonly used combination causes stinging and burning in many people.

Formaldehyde has been another prominent and potent antimicrobial agent; other agents gradually donate or release formaldehyde. Some countries, such as Japan, restrict the use of "formaldehyde-donating" preservative agents, such as imidazolidinyl urea and diazolidinyl urea, and prohibit the use of "formaldehyde-releasing" preservative agents such as Quaternium-15 and DMDM Hydantoin. Other countries, such as the European Union, are not as restrictive about the types of preservative agents that can be employed, however, they limit the concentration of each agent included in a product.

Which preservative agents to incorporate in a product formulation, and the amount of each agent needed, typically varies from one formulation to another. They may be determined empirically by preservative efficacy testing. Despite the expertise and knowledge in the art of formulation, a formulator often must test each combination of preservative agents and adjuvants used in a particular formulation for its effectiveness against a broad range of microorganisms. This is because it is often not well understood why a particular combination of preservative agents and adjuvants is effective. Moreover, given the potential for irritation and sensitization from preservative agents, an additional objective of the formulator is to create a preservative system that does not cause adverse reactions.

Developing a unique, safe and internationally acceptable preservative system is a complex problem that has been addressed by the present invention. The following description of the preservative system is meant to be representative of the overall technology. Anyone skilled in the art of formulation and/or microbiology will see variations and potential applications for this technology beyond the examples listed. Therefore, the invention is not limited to the formulations represented by these examples, but instead covers a variety of formulations.

SUMMARY OF THE INVENTION

An improved preservative system for topically applied cosmetics, skincare products, personal care, over-the-counter (OTC) and pharmaceutical products, such as dermatological, ophthalmic, and otic products, has been discovered that has minimal adverse reactions, and complies with regulations in many countries. This preservative system not only provides significant protection from the potential of microbial contamination, but also has been shown to be free of any significant irritation or sensitization potential associated with preservative systems found in many topically applied products.

The invention is a topical composition that includes a preservative having one or more of benzyl alcohol, disodium EDTA, and a para-hydrobenzoic acid (paraben), in an effective antimicrobial amount, combined with one or more enhancers selected from the group of sorbic acid, salts of sorbic acid, benzoic acid, salts of benzoic acid, and a phospholipid. In particular embodiments, para-hydrobenzoic acid is selected from the group consisting of methylparaben, propylparaben and butylparaben.

In disclosed embodiments, benzyl alcohol is present in a concentration of about 0.5 to 3%, sodium EDTA in a concentration of about 0.05 to 0.15%, and the paraben in a concentration of about 0.01 to 0.4%. In embodiments in which the paraben is present, it comprises one or more of methylparaben at a concentration of about 0.1 to 0.4%, propylparaben at a concentration of about 0.05 to 0.3%, and butylparaben at a concentration of about 0.01 to 0.1%.

In other embodiments, the benzyl alcohol is present in a concentration of about 0.75 to 2%, the disodium EDTA in a concentration of about 0.08 to 0.12%, the methylparaben in a concentration of about 0.18 to 0.28%, propylparaben in a concentration of about 0.08 to 0.22%, and butylparaben in a concentration of about 0.03 to 0.08%.

Particularly useful enhancers of antimicrobial activity have been found to be phospholipids in a concentration sufficient to improve the preservative action of the composition; sorbic acid or one or more of its salts (such as potassium or sodium sorbate) in a concentration sufficient to enhance an antimicrobial action of the composition; and/or benzoic acid or one or more of its salts (such as sodium benzoate) in a concentration sufficient to enhance an antimicrobial action of the composition. When present, the phospholipid (such as Phospholipid CDM) is present in the concentration range of about 0.5 to 1%, the sorbic acid or its salt is present in a concentration range of about 0.3–0.5%, and the sodium benzoate is present in a concentration of about 0.4–1%.

In more particular embodiments, the phospholipid is Phospholipid CDM, which is present in the concentration range of less than about 0.60%, and the benzoate is sodium benzoate, which is present in a concentration of less than about 0.6%.

In other examples, the topical composition includes a base preservative selected from one or more of 0.5 to 3% benzyl alcohol and 0.05 to 0.15% disodium EDTA; and one or more enhancers selected from the group of phospholipid, sorbic acid, potassium sorbate and sodium benzoate, wherein each enhancer that is present is present in a concentration of no more than about 1%, and which in combination with the preservative provides an effective antimicrobial effect. The base preservative may further include 0.1 to 0.4% of para-hydroxybenzoic acid, such as one or more of 0.1 to 0.4% methylparaben, 0.05 to 0.3% propylparaben, and 0.01 to 0.1% butylparaben. Such compositions may include at least 0.5% phospholipid, at least 0.3% sorbic acid, at least 0.4% potassium sorbate, or at least 0.4% sodium benzoate. In particular embodiments, the phospholipid is present in a concentration of about 0.5%, the sorbic acid in a concentration of about 0.3–0.4%, the potassium sorbate in a concentration of about 0.3–0.4%, and the sodium benzoate in a concentration of about 0.4–1%.

In other embodiments, the topical composition comprises, or consists essentially of, a preservative comprising one or more of benzyl alcohol and a salt of ethylene diamine tetracetic acid, and one or more enhancers selected from the group of a phospholipid, sorbic acid, a salt of sorbic acid, benzoic acid, and a salt of benzoic acid, such that the preservative and ehancer are present in an effective antimicrobial amount. In some embodiments, the enhancer is the phospholipid alone, or a combination of the phospholipid and the benzoic acid (including salts of benzoic acid). In other embodiments, the enhancer is the benzoic acid alone (including a salt of benzoic acid alone), or the benzoic acid in combination with the sorbic acid (including a salt of sorbic acid). Alternatively, the enhancer may be sorbic acid alone (or a salt of sorbic acid), or the sorbic acid in combination with a para-hydrobenzoic acid preservative. In yet other embodiments, the preservative base includes both the benzyl alcohol and the EDTA.

The composition may also include one or both of the benzyl alcohol and the EDTA, in combination with the phospholipid, benzyl alcohol, sorbic acid, and a para-hydrobenzoic acid preservative.

In other embodiments, the composition includes benzyl alcohol and sorbic acid; benzyl alcohol, disodium EDTA, potassium sorbate, and a para-hydrobenzoic acid preservative; benzyl alcohol, disodium EDTA, phospholipid, and sodium benzoate; sodium benzoate, disodium EDTA, potassium sorbate, and an effective amount of a para-hydrobenzoic acid preservative; disodium EDTA and potassium sorbate; and benzyl alcohol, disodium EDTA, the phospholid, sorbic acid, and a para-hydrobenzoic acid preservative, optionally including sorbic acid or potassium sorbate.

The compositions are preferably substantially free of preservative amounts of chlorphenesin or phenoxyethanol, which the present inventors have found to cause skin irritation in a substantial number of test subjects.

The preservative systems of the present invention may be used in oil-in-water emulsions, water-in-oil emulsions, water based formulations, water based formulation containing high levels of surfactants, and liposomal suspensions, among others. Varying formulations of the preservative system have been found to be most suitable for these different types of compositions, as explained in the following detailed description.

DETAILED DESCRIPTION OF SEVERAL EMBODIMENTS

The present invention involves several new combinations of preservative agents that have been identified that not only exhibit significant preservative efficacy, but simultaneously have been shown to be safe in use. These preservative combinations are also acceptable to regulatory agencies in many jurisdictions, for example the U.S., European Economic Community and Japan, and are effective against gram positive and gram negative bacteria, yeast and molds.

EXAMPLE 1

The following test method was employed to evaluate the effectiveness of the preservative system in the formulations tested. This method is an adaptation of the method prescribed by the *United States Pharmacopeia* (USP) Twentieth Revision (1980) and the Cosmetic, Toiletry and Fragrance Association (*A Guideline for the Determination of Adequacy of Preservation of Cosmetics and Toiletry Formulations*).

The Bacterial Challenge/Rechallenge Procedure was performed as follows:

1. Dispensed 40 grams of product into sterile sample jars.
2. Removed six separate bacterial cultures (Pseudomonas aeruginosa ATCC 15442, Eschericia coli ATCC 8739, Staphylococcus aureus ATCC 6538, Proteus mirabilis [product isolate], Pseudomonas cepacia [ATCC 25416]) from liquid nitrogen storage. Each culture was thawed for 20 minutes at 37° C.
3. The thawed cultures were pooled, and sufficient sterile saline added to make a suspension yielding a final concentration of $10^8$ bacteria per milliliter of each microorganism. The bacterial count of pooled microorganisms was confirmed using Letheen broth diluent and TSALT (Typticase Soy Agar with Lecithin and Polysorbate 80$^a$) plates. The organisms were incubated while inverted at 37° C. for 48 hours.

$^a$TSALT from Difco or equivalent composed of 15 g/l casein peptone, 5 g/l soy peptone, 5 g/l sodium chloride, 0.7 g/l lecithin, 5 g/l Polysorbate 80 and 20 g/l of agar. Made to a final pH of 7.3±0.2. Heat to boiling and autoclave before use.

4. The test product was inoculated with 0.2 milliliters of the pooled bacterial suspension to achieve a final concentration of $10^5$ to $10^6$ bacteria per gram.
5. The test product was mixed thoroughly with a tongue depressor and incubated loosely covered at room temperature.
6. At 0, 2 and 7 days, the number of each microorganism in the test product was counted in the following manner:

Using a sterile tongue depressor or transfer tube, the test product was mixed thoroughly.
One milliliter of the test product was withdrawn with a transfer tube and deposited into 9 milliliters of Letheen broth.
Serial transfers into Letheen broth were performed to obtain dilutions of $10^{-1}$, $10^{-2}$ and $10^{-3}$.
Dispensed 1 milliliter of each dilution into labeled petri plates.
Poured 15 milliliters of tempered TSALT on to these plates and swirled for good dispersion.
Cooled plates and incubated inverted at 37° C.
Counted bacterial concentration (organisms per gram) after 48 hours incubation and record results.
Rechallenge the test product that does not show detectable levels of bacterial growth after 7 days of testing.

The Bacterial Rechallenge procedure was performed as follows:

1. A pooled bacterial suspension was prepared as above and the test product re-inoculated with 0.05 milliliter aliquots of the bacterial suspension.
2. The test product was mixed thoroughly with a tongue depressor and incubated loosely covered at room temperature.
3. At 0, 2, 7, 14 and 28 days after re-inoculation, the microorganisms were counted in the test product as shown in step # 6 in the above bacterial challenge procedure.

B. Yeast Challenge/Rechallenge Procedure

Yeast Challenge

1. Dispensed 40 grams of test product into sterile sample jars.
2. Removed the yeast culture (Candida albicans ATCC 10231) from liquid nitrogen storage, and thawed for 20 minutes at 37° C.
3. The thawed culture was added to enough sterile saline to make a suspension yielding a final concentration of $10^8$ yeast per milliliter. The count of yeast was confirmed using Letheen broth diluent and PDAT (Potato Dextrose Agar with Lecithin and Polysorbate 80$^b$) plates. The culture was incubated inverted at 25° C. for 5 days.

$^b$PDALT composed of 200 g/l potato infusion, 20 g/l dextrose, 0.7 g/l lecithin, 5 g/l Polysorbate 80 and 15 g/l of agar. Heat to boiling and autoclave. Prior to use, add 2.0 milliliters of antibiotic solution per 100 milliliters of media and mix prior to use.

4. Inoculated the test product with 0.2 milliliters of the yeast suspension in order to achieve a final concentration of $10^5$ to $10^6$ yeast per gram.
5. Mixed thoroughly with a tongue depressor and incubate loosely covered at room temperature.
6. At 0, 2 and 7 days, counted the number of organism in the test product in the following manner:

Using a sterile tongue depressor or transfer tube, the test product was mixed thoroughly.
Withdrew one milliliter of the test product with a transfer tube and deposited it into 9 milliliters of Letheen broth.
Serially transferred into Letheen broth to obtain dilutions of $10^{-1}$, $10^{-2}$ and $10^{-3}$.
Dispensed 1 milliliter of each dilution into labeled petri plates.
Poured 15 milliliters of tempered PDALT on to plates and swirled for good dispersion.
Cooled plates and incubated inverted at 25° C.
Counted plates after 5 days incubation by determining yeast concentration per gram.

Rechallenged each test product that did not show detectable levels of yeast growth after 7 days of testing.

Yeast Rechallenge Procedure

1. Prepared the yeast suspension as above and re-inoculated the test product with 0.1 milliliter aliquots of the yeast suspension.
4. Mixed the test product thoroughly with a tongue depressor and incubated loosely covered at room temperature.
5. At 0, 2, 7, 14 and 28 days after re-inoculation, counted the yeast remaining in the test product as shown in step # 6 in the above yeast challenge procedure.

C. Mold Challenge/Rechallenge Procedure

Mold Challenge

1. Dispensed 40 grams of product into sterile sample jars.
2. Pooled the three separate mold cultures (Penecillium Funiculosum ATCC 11797, Penecillin corylophilum ATCC 9784 and Aspergillus niger ATCC 16404) by mixing approximately 2 milliliters of each mold solution to obtain a suspension yielding a final concentration of $10^8$ mold per milliliter.
3. Inoculated the test product with 0.2 milliliters of the mold suspension in order to achieve a final concentration of $10^5$ to $10^6$ mold per gram of test product. Counted the mold inoculum using Letheen broth diluent and PDALT$^b$ plates. Incubated at 25° C. for 5 days.

$^b$PDALT composed of 200 g/l potato infusion, 20 g/l dextrose, 0.7 g/l lecithin, 5 g/l Polysorbate 80 and 15 g/l of agar. Heat to boiling and autoclave. Prior to use, add 2.0 milliliters of antibiotic solution per 100 milliliters of media and mix prior to use.

4. Mixed thoroughly with a tongue depressor and incubated loosely covered at room temperature.
5. At 0, 1, 2 and 7 days, counted the number of each microorganism in the test product in the following manner.
   Using a sterile tongue depressor or transfer tube, mixed the test product thoroughly.
   Withdrew one milliliter of the test product with a transfer tube and deposited it into 9 milliliters of Letheen broth.
   Serially transferred the test product into Letheen broth to obtain dilutions of $10^{-1}$, $10^{-2}$ and $10^{-3}$ mold per gram.
   Dispensed one milliliter of each dilution into labeled petri plates.
   Poured 15 milliliters of tempered PDALT with antibiotics onto the plates and swirled for good dispersion.
   Cooled plates and incubated inverted at 25° C.
   Counted plates after 5 days incubation and recorded results.
   Rechallenged the test products that showed less than 5000 mold organisms per gram after 7 days of testing.

Mold Rechallenge

1. Prepared a pooled mold suspension as above and re-inoculated the test product with 0.2 milliliter aliquots of the mold suspension. Counted the mold suspension as described above.
2. Mixed thoroughly with a tongue depressor and incubated loosely covered at room temperature.
3. At 0, 1, 2, 7 and 28 days after re-inoculation, counted the microorganisms in the test product as shown in step # 4 above for the mold challenge procedure.

The acceptance criteria for challenge and rechallenge are shown below:

Acceptance Criteria for Challenge and Rechallenge Tests

Bacterial and Yeast Challenge Tests

Acceptable Results
  Bacterial and yeast levels reduced to less than 10 organisms per gram by 7 days.
Unacceptable Results
  Bacterial and yeast levels greater than 10 organisms per gram at 7 days.

Bacterial and Yeast Rechallenge Tests

Acceptable Results
  Bacterial and yeast levels reduced to less that 10 organisms per gram from 7 through 28 days.
Unacceptable Results
  Bacterial and yeast levels greater than 10 organisms per gram between 7 and 28 days.

Mold Challenge Results

Acceptable Results
  Mold levels reduced to less than 5,000 organisms per gram by 7 days.
Unacceptable Results
  Mold levels greater than 5,000 organisms per gram though 7 days.

Mold Rechallenge Results

Acceptable Results
  Mold levels reduced to less than 5,000 organisms per gram by 7 days and less than 1,000 organisms per gram by 28 days.
Unacceptable Results
  Mold levels greater than 5,000 organisms per gram from days 7 through 28 or less than 5,000 organisms per gram by 7 days and greater than 1,000 organisms per gram by 28 days.

EXAMPLES 2–12

Oil-In-Water Emulsion System

The following oil-in-water emulsion formulations were developed and then tested using the methods of Example 1, both initially and after storage of the formulation for one month at 50° C. This example covers a broad range of cosmetic, skincare, personal care, and pharmaceutical preparations. An oil-in-water emulsion is an emulsion in which water is the continuous phase and oil is the disperse phase.

| Ingredients | Percentage (w/w) |
| --- | --- |
| Deionized Water | 48.4 |
| Sunscreen Mixture (a) | 13.0 |
| Humectants (b) | 7.0 |
| Emulsifiers (c) | 6.0 |
| Emollients (d) | 11.3 |
| Vitamins, Herbal and Natural Ingredients (e) | 11.5 |
| Thickeners (f) | 0.2 |
| Deionized Water and/or Butylene Glycol | 2.6 |
| and Preservative System | |
| Total | 100.0 |

(a) A combination of octyl methoxycinnamate (Parsol MCX from Hoffmann-La Roche of Nutley, N.J.), Benzophenone-3 (SpectraSorb UV-9 from Cytec of Wayne, N.J.), a titanium dioxide disperson (a dispersion of titanium dioxide in octyl palmitate, alumina and polyhydroxysteatic acid sold under the trademark of Tioveil OP by Tioxide of, NJ) and a zinc oxide (a dispersion of zinc oxide in octyl palmitate and polyhydroxystearic acid sold under the trademark of Spectraveil OP by Tioxide of, NJ) in sufficient quantities to produce a Sun Protection Factor (SPF) value of 15. Each ingredient may be between 0 and 100% of the formula input amount.

(b) A combination of humectants consisting of glycerin, butylene glycol and panthenol. Each ingredient may be between 0 and 100% of the formula input amount.

(c) A combination of emulsifiers consisting of glyceryl stearate with PEG-100 stearate (Lexemul 561 from Inolex Chemical Co. of Philadelphia, Pa.) and stearamine oxide. Each ingredient may be between 0 and 100% of the formula input amount.

(d) A combination of emollients consisting of cetearyl octanoate, cyclomethicone, glyceryl polymethacrylate, dimethicone, cetyl alcohol and stearyl alcohol.

(e) A combination of vitamins, herbal and natural ingredients consisting of magnesium ascorbyl phosphate, Fagus sylvatica (beech tree bud) extract, vitamin E acetate, beta glucan, Saxifraga solonifera (strawberry geranium) extract, grape extract, mulberry root extract, Scutellaria (scull cap) root extract, dipotassium glycyrrhizinate, vitamin A palmitate, grape seed extract and superoxide dismutase. Each ingredient may be between 0 and 100% of the formula input amount.

(f) Either xanthan gum, acacia gum or locust bean gum. Each ingredient may be between 0 and 100% of the formula input amount.

The composition of the preservative systems tested and the results of the preservative efficacy testing for these examples is shown in Table 1. This oil-in-water emulsion system required a significant number of preservative agents to pass the test as an acceptable preservative system. Examples 6 though 12 were not adequately preserved according to the test procedure listed above, because they failed to adequately prevent the growth of yeast or mold, or both. Furthermore, Examples 4 and 5, which are the same formulation tested initially and after storage for 1 month at 50° C., was found to be unacceptable because the elevated storage temperature (50° C.) adversely affected the preservative system. Only Examples 2 and 3 were found to be adequately preserved. Storage at elevated temperatures (50° C.) did not adversely affect the preservative system in these formulas (data not shown).

The presence of the phospholipid preservative at a concentration of 0.5% by weight, in combination with at least 0.3% of the sorbate (in the form of sorbic acid), and 0.1% of the EDTA salt (in the form of disodium EDTA) provided adequate preservation of the oil-in-water emulsion that also included 1% of benzyl alcohol and at least about 0.5% of one or more parabens (such as at least about 0.25% methylparaben, 0.2% propylparaben, and 0.05% butyl paraben). Certain particularly effective compositions included about 0.5% phospholipid (in the form of phospholipid CDM), 1% benzyl alcohol, 0.1% EDTA (in the form of disodium EDTA), 0.3–0.4% sorbate (in the form of sorbic acid), and 0.5–0.75% of the paraben.

The following examples give general ranges of ingredients for each test formulation. However, the specific formulations of each test product are given in Table 6.

EXAMPLES 13–21

Water-In-Oil Emulsion

The following water-in-oil emulsion formulations were developed and then tested (using the procedures of Example 1) both initially, and after storage for one month at 50° C. Although this example may seem somewhat specific, it covers a broad range of cosmetic, skincare, personal care, OTC pharmaceutical, dermatological and prescription pharmaceutical preparations.

| Ingredients | Percentage (w/w) |
| --- | --- |
| Deionized Water | 62.3 |
| Sunscreen Mixture (g) | 12.0 |
| Humectants (h) | 7.0 |
| Emulsifiers (i) | 0.2 |
| Emollients (j) | 15.6 |
| Vitamins, Herbal and Natural Ingredients (k) | 0.2 |
| Thickeners (l) | 0.3 |
| Deionized Water and/or Butylene Glycol and Preservative System | 2.4 |
| Total | 100.0 |

(g) A combination of octyl methoxycinnamate (Parsol MCX from Hoffmann-La Roche of Nutley, N.J.), Benzophenone-3 (SpectraSorb UV-9 from Cytec of Wayne, N.J.), a dispersion of titanium dioxide in octyl palmitate, alumina and polyhydroxysteatic acid (a dispersion of titanium dioxide sold under the trademark of Tioveil OP by Tioxide of NJ) and a zinc oxide dispersion in octyl palmitate and polyhydroxyisostearic acid (a dispersion of zinc oxide in octyl palmitate and polyhydroxystearic acid sold under the trademark of Spectraveil OP by Tioxide of, NJ) in sufficient quantities to produce a Sun Protection Factor (SPF) value of 30. Each ingredient may be between 0 and 100% of the formula input amount.

(h) A combination of humectants consisting of butylene glycol and panthenol. Each ingredient may be between 0 and 100% of the formula input amount.

(i) A combination of emulsifiers consisting of a mixture of polyglyceryl-4 isostearate, cetyl dimethicone copolyol and hexyl laurate (sold under the trademark of Abil WE09 by Goldschmidt Chemical Co. of NJ) and cetyl dimethicone copolyol (sold under the trademark of Abil EM90 by Goldschmidt Chemical Co. of NJ). Each ingredient may be between 0 and 100% of the formula input amount.

(j) A combination of emollients consisting of C12–15 alkyl benzoate, octyl palmitate, cycolmethicone, cetyl dimethicon, hydrogenated castor oil and phenyl trimethicone. Each ingredient may be present between 0 and 100% of the formula input amount.

(k) A combination of vitamins, herbal and natural ingredients consisting of magnesium ascorbyl phosphate, vitamin E acetate, beta glucan, vitamin A palmitate, grape seed extract and superoxide dismutase. Each ingredient may be between 0 and 100% of the formula input amount.

(l) Either sodium chloride and microcrylstalline wax. Each ingredient may be between 0 and 100% of the formula input amount.

The composition of the preservative systems tested, and the results of the preservative efficacy testing for these examples, is shown in Table 2. The water-in-oil emulsion system of Examples 13–21 required a smaller number of preservative agents to pass the test as an acceptable preservative system than those for Examples 2 through 12. Examples 18 though 21 were not adequately preserved according to the test procedure listed above, because they failed to pass one or more of the organism challenges. However, Examples 13, 15 and 17 were found to be adequately initially preserved. Storage at elevated temperatures, a shown in Example 14 (same formula as Example 13) and Example 16 (same formula as Example 15) did not adversely affect the preservative system in these formulas.

For the water-in-oil emulsion, the presence of at least about 1% benzyl alcohol, at least about 0.1% of the EDTA salt (in this case disodium EDTA), at least about 0.4% of the sorbate (in the form of potassium sorbate), and at least about 0.35% of the parabens (such as at least about 0.2% methyl paraben, 0.1% propylparaben, and 0.05% butylparaben) adequately preserved Examples 13–17. These examples contained benzyl alcohol in the range of about 1–1.5%, about 0.1% disodium EDTA, 0.4% potassium sorbate, and 0.35–0.4% paraben or parabens.

EXAMPLES 22–32

Water Based Liquid

The following water based liquid formulation variants were developed and tested using the above test method both initially and after storage for one month at 50° C. A water based liquid is a liquid that is not an emulsion, and in which the primary ingredient is water (for example a liquid that is 70% or more water). Such products could include a skin toner, a solution of a drug, toilet water, skin tonic, scalp preparation, etc.

| Ingredients | Percentage (w/w) |
| --- | --- |
| Deionized Water | 92.4 |
| Humectants (m) | 0.7 |
| Emulsifiers (n) | 2.0 |
| Vitamins, Herbals and Natural Ingredients (o) | 2.3 |
| Fragrance (p) | 0.1 |
| Deionized Water and/or Butylene Glycol | 2.5 |
| and Preservative System | |
| Total | 100.0 |

(m) A combination of humectants consisting of butylene glycol and panthenol. Each ingredient may be between 0 and 100% of the formula input amount.

(n) An emulsifier chosen from the group polysorbate 20, 40, 60 and 80. A combination of these ingredients may also be used in any proportion between 0 and 100% of the formula input amount.

(o) A combination of vitamins, herbal and natural ingredients consisting of magnesium ascorbyl phosphate, vitamin E acetate, beta glucan, vitamin A palmitate, grape seed extract, superoxide dismutase, menthol, bisabolol and phytic acid. Each ingredient may be between 0 and 100% of the formula input amount.

(p) A fragrance composition containing either natural, synthetic or a combination of natural and synthetic components.

The composition of the preservative systems tested and the results of the preservative efficacy testing for these examples is shown in Table 3. These water-based liquid formulations are relatively easier to preserve, and do not require as many preservative agents to pass the test as an acceptable preservative system. Example 32 was not found to be adequately preserved according to the test procedure listed above. Examples 22, 24, 26 and 28 through 31 were found to be acceptably preserved according to the criteria listed above. Furthermore, storage at elevated temperatures did not adversely affect the preservative system as witnessed by the fact that the identical system stored at 50° C. were found to pass the preservative efficacy test (the pairs of identical formulas tested initially and after 1 month storage at 50° C. are Examples 22 and 23, Examples 24 and 25, Examples 26 and 27).

Table 3 illustrates that for certain specific examples of the water based liquids, adequate preservatives included at least about 0.5% phospholipid, 0.95% benzyl alcohol, 0.1% EDTA (in the form of disodium EDTA), 0.4% of the benzoate (in the form of sodium benzoate), and in the substantial absence of any paraben preservative. In other embodiments, there was at least 0.5% of the phospholipid, 0.5% benzyl alcohol, 0.5% phenoxyethanol, 0.1% of the EDTA, and 0.4% of the benzoate. In yet other embodiments, the preservative system did not include the phospholipid or benzyl alcohol, but did include about at least 0.15% chlorphenesin, 1% phenoxyethanol, and 0.1% of the EDTA in combination with either about: 0.15% of one of the parabens and 0.15% of a paraben (such as methylparaben); or about 0.4% of the sorbate or 1% of the benzoate, and 0.15% of the paraben.

In particular embodiments, the preservative system included about 0.5% of the phospholipid, 0.5–1% benzyl alcohol, 0.15% chlorphenesin, 0.5–1% phenoxyethanol, 0.1% of the EDTA, about 0.4% of the sorbate (in the form of potassium sorbate), 0.4–1% of the benzoate (in the form of sodium benzoate), and/or 0.15% of the paraben (in the form of methylparaben).

EXAMPLES 33–43

Water Based Liquids Containing High Level of Surfactants

The following skin cleanser formulation variants were developed and tested using the test method of Example 1, and the formulations were tested both initially and after storage for one month at 50° C. As in the other examples, this formulation was developed to test for a broad range of cosmetic, skincare, personal care, OTC pharmaceutical, dermatological, otic and prescription pharmaceutical preparations. However, this test formulation contained a high level of surfactants (at least 5% surfactants, for example 5–50% surfactants). The surfactants in the following formula are the emulsifiers, which are 7.5% of the formulation. The surfactants that are useful for water based liquids may be non-ionic, anionic, cationic or amphoteric. These surfactants include (without limitation) all manner of ethoxylated or propylated surface active agents regardless of the degree of ethoxylation. There is no limitation on the number of surfactants that may be used, although typically there are 1 to 5 surfactants in the composition.

| Ingredients | Percentage (w/w) |
| --- | --- |
| Deionized Water | 52.4 |
| Humectants (q) | 6.0 |
| Emulsifiers (r) | 7.5 |
| Emollients (s) | 31.0 |
| Vitamins, Herbal and Natural Ingredients (t) | 0.7 |
| Thickening Agents (u) | 0.2 |
| Fragrance (v) | 0.1 |

| Ingredients | Percentage (w/w) |
|---|---|
| Neutralizing Agents (w) | 0.7 |
| Deionized Water and/or Butylene Glycol | 2.4 |
| and Preservative System | |
| Total | 100.0 |

(q) A combination of humectants consisting of glycerin, sorbitol, butylene glycol and panthenol, wherein each ingredient may be between 0 and 100% of the formula input amount.

(r) A combination of emulsifiers consisting of a mixture of glyceryl stearate and ceteareth 20, wherein each ingredient may be between 0 and 100% of the formula input amount.

(s) A combination of emollients consisting of tridecyl stearate, tridecyl trimellitate, depentaerythrityl hexacaprylate/hexacaprate, caprylic/capric triglyceride, isocetyl stearate, stearyl alcohol and cetyl alcohol. Each ingredient may be present between 0 and 100% of the formula input amount.

(t) A combination of vitamins, herbal and natural ingredients consisting of magnesium ascorbyl phosphate, vitamin E acetate, beta glucan, vitamin A palmitate, grape seed extract and superoxide dismutase. Each ingredient may be between 0 and 100% of the formula input amount.

(u) A fragrance composition containing either natural, synthetic or a combination of natural and synthetic components.

(v) A combination of carbomer and acrylates/C10–30 alkyl acrylate crosspolymer. Each ingredient may be between 0 and 100% of the formula input amount.

(w) A neutralizer chosen from the group of triethanolamine, sodium or potassium hydroxide and amino acids or a combination of these ingredients where each ingredient may be between 0 and 100% of the formula amount.

The composition of the preservative systems tested, and the results of the preservative efficacy testing for these formulations, are shown in Table 4. These water-based liquid formulations, containing a high level of surfactants, are somewhat difficult to preserve. Only Example 41 was found to be inadequately preserved using the test procedure of Example 1, while Examples 33, 35, 37, 39 and 42 were found to be acceptably preserved at room temperature according to those same criteria. Furthermore, storage at elevated temperatures did not adversely affect the preservative system as witnessed by the fact that each identical system stored at 50° C. was found to pass the preservative efficacy test (the pairs of identical formulas tested initially and after 1 month storage at 50° C. are Examples 33 and 34, Examples 35 and 36, Examples 37 and 38, Examples 39 and 40 as well as Examples 42 and 43).

Although Examples 35 and 36 were found to be acceptably preserved, the combinations of preservative agents contained in these formulations were found to discolor the product after storage for one month at 50° C., which is undesirable in spite of the formulation's ability to inhibit microbial growth. The only substantial difference between Examples 33 and 34 (which did not discolor the composition) and Examples 35 and 36 (which did discolor) was the presence of 0.4% potassium sorbate instead of 0.4% sorbic acid. Hence in compositions containing a high level of surfactants, the use of sorbic acid is preferred instead of a salt of sorbic acid (such as potassium sorbate).

In particular embodiments of the water-based, high surfactant composition, there was at least about 0.95–1% benzyl alcohol, in combination with about 0.5% phospholipid, usually in combination with EDTA, sorbic acid and a paraben. In particular examples, there is about 0.5% phospholipid, 1% benzyl alcohol, 0.1% EDTA (in the form of disodium EDTA), 0.3–0.4% sorbic acid (preferably not in the form of a salt of sorbic acid), and at least about 0.35% of a paraben (such as one or more of methylparaben, propylparaben and/or butylparaben). In other examples, there is at least about 0.5% phospholipid in combination with about 1% phenoxyethanol, 0.1% EDTA, 0.3% sorbic acid, and 0.35% paraben, however compositions that contain this amount of phenoxyethanol are not preferred because the inventors have determined that they cause skin irritation.

EXAMPLES 44–53

Water Based Liposomal Suspension

The liposomal suspension formulations shown in Table 5 were tested using the test method of Example 1. Liposomes are smectic mesomorphs that form spontaneously by polar lipids in aqueous media, so that the lipid molecules are arranged in concentric bilayers, with hydrophobic tails pointing away from the aqueous compartment. The preservative systems were tested initially, and then after storage for one month at 50° C. A formulation was developed that covered a broad range of cosmetic, skincare, personal care, OTC pharmaceutical, dermatological, otic and prescription pharmaceutical preparations.

| Ingredients | Percentage (w/w) |
|---|---|
| Deionized Water | 76.4 |
| Humectants (x) | 11.0 |
| Liposomal Preparations (y) | 9.0 |
| Thickeners (z) | 0.7 |
| Neutralizers (aa) | 0.5 |
| Deionized Water and/or Butylene Glycol | 2.4 |
| and Preservative System | |
| Total | 100.0 |

(x) A combination of humectants consisting of glycerin, butylene glycol and glyceryl polymethacrylate, and PEG-75. Each ingredient may be between 0 and 100% of the formula input amount.

(y) A combination of liposomal preparations consisting of a liposomal preparation of live yeast cell derivative (composed of water, live yeast cell derivative and lecithin sold as Dermasome TRF from Brooks Industries of NJ) and a liposomal preparation of panthenol (composed of water, lecithin and panthenol sold as Dermsome P from Brooks Industries of NJ). Each of these liposomal preparations may be incorporated separately between 0 and 100% of the formula input amount.

(z) A combination of thickeners consisting of a carbomer and xanthan gum. Each ingredient may be present between 0 and 100% of the formula input amount.

(aa) A neutralizer chosen from the group of triethanolamine, sodium or potassium hydroxide and amino acids or a combination of these ingredients where each ingredient may be between 0 and 100% of the formula amount.

The composition of the preservative systems tested, and the results of the preservative efficacy testing for these examples, is shown in Table 5. The water-based liposomal formulations were somewhat difficult to preserve, and several preservative agents were ideally present to maximize the acceptability of the preservative system. Example 50 was found to be inadequately preserved according to the test procedure listed above. Examples 44, 46, 48, 51 and 52 were found to be acceptably preserved according to the criteria in Example 1, because it did not eliminate the growth of mold on rechallenge. Moreover, storage at elevated temperatures did not adversely affect the preservative system as witnessed by the fact that each identical system stored at 50° C. passed the preservative efficacy test (the pairs of identical formulas tested initially and after 1 month storage at 50° C. are Examples 44 and 45, Examples 46 and 47, Examples 48 and 49 as well as Examples 52 and 53).

In particular embodiments, the preservative system for the liposomal preparation includes either benzyl alcohol or phenoxyethanol, in combination with either phospholipid or a benzoic acid (such as sodium benzoate), in combination with an effective amount of EDTA (such as 0.1% disodium EDTA) and one or more parabens (such as 0.35% paraben, for example 0.2% methylparaben, 0.1% propylparaben, and 0.05% butylparaben). The formulations also optionally include chlorphenesin or sorbic acid (such as its potassium salt). In particular examples, the formulations include about 0.5% phospholipid, 1% benzyl alcohol, 0.15–0.26% chlorphenesin, 1% phenoxyethanol, 0.1% disodium EDTA, 0.4% potassium sorbate, and 0.35–0.6% paraben (such as 0.2–0.45% methylparaben, 0.1% propylparaben, and 0.05% butylparaben). However, in particularly preferred embodiments, the composition is substantially free of preservative amounts of chlorphenesin and phenoxyethanol, which the inventors have found to irritate the skin of an unacceptable number of test subjects.

EXAMPLE 54

Safety Testing

Safety testing was conducted on each of the formulations listed above that were found to be acceptably preserved. This testing included cell culture testing, repeat insult patch testing and in-use human safety testing. The results of the cell culture testing, and particularly the repeat insult patch testing, found no irritation or allergic sensitization problems. However, during initial in-use safety testing, the subjects reported significant irritation from the use of the formulations listed as Examples 3, 4, 15, 26, 28, 29, 30, 31, 37, 42, 48, 51 and 52. Those reactions were characterized by noticeable stinging and burning sensations. All of these formulations are characterized by the presence of either chlorphenesin or phenoxyethanol. Diagnostic testing conducted on the subjects reporting these reactions confirmed that these ingredients were the source of the stinging and burning reactions reported during the in-use testing. Many of the preservative systems that failed microbiological testing also contained one or the other of these preservatives. Therefore, the preferred embodiments of the composition are substantially free of chlorphenesin or phenoxyethanol. A composition that is "substantially free" of chlorphenesin contains less than about 0.05% of chlorphenesin, and a composition that is "substantially free" of phenoxyethanol contains less than about 0.1% of phenoxyethanol. A composition that is "free" of these ingredients does not contain any detectable ingredient.

Additional in-use safety testing conducted more than 500 subjects for periods of at least one month (and as long as three months in some cases) of twice daily usage revealed that the formulations determined to be safe by the above procedure were indeed safe during extended use.

EXAMPLE 55

Testing conducted both for preservative efficacy and safety have revealed that a safe, effective preservative system in accordance with this invention can provide a variety of topically applied products using a combination of benzyl alcohol, disodium EDTA, methylparaben, propylparaben and butylparaben augmented with Phospholipid CDM, sorbic acid, potassium sorbate or sodium benzoate as appropriate. The concentration range of these preservative agents as witnessed by the results from the above tests are shown in Table 7.

The most preferred concentration ranges for the preservative systems are as follows: benzyl alcohol: 0.75 to 1.75%; disodium EDTA: 0.08 to 0.12%; methylparaben: 0.18 to 0.28%; propylparaben: 0.08 to 0.22%; butylparaben: 0.03 to 0.08. As necessary to pass the microbiological testing of Example 1, these preservative agents may be combined with any one of the following preservative agents (or combinations of these agents): Phospholipid CDM: 0.00 to 0.60%; sorbic acid: 0.00 to 0.50%; potassium sorbate: 0.00 to 0.50%; or sodium benzoate: 0.00 to 0.60%.

Compositions of the present invention have also been made in accordance with the ranges of concentrations of preservatives set forth in Table 7.

TABLE 7

Preferred Combinations of Preservative Agents

| Preservative Agent | Preferred Use Concentration | Found in Examples |
|---|---|---|
| Benzyl Alcohol | 0.50 to 3.00% | 2, 13, 17, 22, 24, 33, 39, 44 and 46 |
| Disodium EDTA | 0.05 to 0.15% | 2, 13, 17, 22, 24, 33, 39, 44 and 46 |
| Methylparaben | 0.10 to 0.40% | 2, 13, 17, 22, 24, 33, 39, 44 and 46 |
| Propylparaben | 0.05 to 0.30% | 2, 13, 17, 22, 24, 33, 39, 44 and 46 |
| Butylparaben | 0.01 to 0.10% | 2, 13, 17, 22, 24, 33, 39, 44 and 46 |
| Phopholipid CDM | 0.0 to 1.00% | 2, 22, 24, 33, 39, 44 and 46 |
| Sorbic Acid | 0.0 to 1.00% | 2, 33 and 39 |
| Potassium Sorbate | 0.0 to 1.00% | 13 and 17 |
| Sodium Benzoate | 0.0 to 1.00% | 22, 23, 44 and 46 |

The combinations of preservative agents in accordance with this invention are safe and effective in a broad class of formulations, which is not only unique but also very unexpected given the breadth of product types that have been evaluated.

EXAMPLE 56

Antimicrobial Phospholipid

Several of the formulations in accordance with this invention include a phospholipid, which upon hydrolysis yields phosphoric acid, an alcohol, a fatty acid, and a nitrogenous base. The phospholipids of the present invention are preferably biomimetic antimicrobial phospholipid complexes, such as those manufactured by Mona Industries, or Paterson, N.J., and in particular Phospholipid CDM (coco phosphatidyl propylene glycol-dimonium chloride). Other suitable phospholipids include Phospholipid PTC, Phospholipid ERA, Phospholipid SV, Phospholipid PTS, Phospholipid PTL, and Phospholipid GLA, all available from Mona Industries. Examples of such phospholipid agents are disclosed more fully in U.S. Pat. Nos. 4,209,449, 4,503,002, 5,215,976 and 5,286,719, which are incorporated by reference. The phospholipids made in accordance with that patent may be represented by the following general formula:

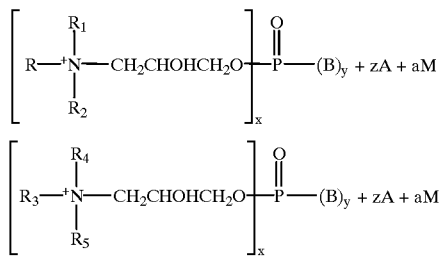

where:

x=1 to 3 or mixtures thereof;

x+y=3;

z=x;

a=0 to 2;

B=O or OM;

A=Anion;

M is a cation;

R, $R_1$ and $R_2$ are the same or different and are alkyl, substituted alkyl, alkyl aryl or alkenyl groups of up to 16 carbon atoms with the provisio that the total carbon atoms in $R+R_1+R_2$ is between 10 and 24; or where R can be an amidoamine moiety of the formula

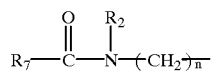

wherein n is an integer from about 2 to 6, $R_4$ and $R_5$, which may be the same or different, are selected from alkyl, hydroalkyl, carboxyalkyl or up to 6 carbon atoms in each alkyl moiety, and polyoxalkylene of up to 10 carbon atoms; in addition R4 and R5 taken together with the nitrogen to which they are attached may represent an N-heterocycle;

R6 is hydrogen or alkyl, hydroxyalkyl or alkenyl of up to 6 carbon atoms each or cycloalkyl of up to 6 carbon atoms, preferably of from 2 to 5 cargon atoms, or polyoxyalkylene of up to 10 carbon atoms;

R7 is alkyl, alkenyl, alkoxy or hydroxyalkyl of from 5 to 21 carbon atoms each, or aryl or alkaryl of up to 20 carbon atoms;

or wherein substituents are as further defined in the incorporated patents.

Examples of phospholipids that may be used in this invention are phospholipids that are soluble in water, and have a chain length of the lipid portion that is 12 to 18 carbons in length (such as C12–18 alkyl, for example straight chain alkyl). Such examples also ideally have a positively charged amine, that more esaily attaches itself to the anionic surface of a microorganism. The amine functionality is preferably a quaternary ammonium.

An "effective antimicrobial mount" of an ingredient is an amount sufficient to pass the tests of Example 1 for evaluating the effectiveness of the preservative systems. A "sorbate" includes both sorbic acid and a salt of sorbic acid. A "benzoate" includes both benzoic acid and a salt of benzoic acid. "EDTA" refers to ethylene diamine tetracetic acid.

TABLE 1

Preservative Agents and Test Results for an Oil-in-Water Emulsion

| Example No. | Storage Time & Temperature | Phospholipid CDM | Benzyl Alcohol | Chlorphenesin | Phenoxyethanol | Disodium EDTA | Sorbic Acid | Potassium Sorbate | Methylparaben | Propylparaben | Butylparaben | Water and/or Butylene Glycol | Micro Results | |
|---|---|---|---|---|---|---|---|---|---|---|---|---|---|---|
| | | | | | | | | | | | | | Challenge | Rechallenge |
| Example 2 | 0 Months/RT | 0.50 | 1.00 | — | — | 0.10 | 0.40 | — | 0.25 | 0.20 | 0.05 | 0.10 | Pass | Pass |
| Example 3 | 0 Months/RT | 0.50 | 1.00 | 0.04 | — | 0.10 | 0.30 | — | 0.29 | 0.30 | 0.05 | 0.02 | Pass | Pass |
| Example 4 | 0 Months/RT | — | 1.00 | 0.15 | — | — | 0.30 | — | 0.40 | 0.30 | 0.05 | 0.40 | Pass | Pass |
| Example 5 | 1 Month/50° C. | — | 1.00 | 0.15 | — | — | 0.30 | — | 0.40 | 0.30 | 0.05 | 0.40 | Failed for Mold | Not Tested |
| Example 6 | 0 Months/RT | — | 1.00 | 0.15 | — | — | 0.30 | — | 0.25 | 0.10 | 0.05 | 0.75 | Failed for Mold | Not Tested |
| Example 7 | 0 Months/RT | — | 1.50 | — | — | 0.10 | 0.30 | — | 0.20 | 0.10 | 0.05 | 0.35 | Failed for Mold | Not Tested |
| Example 8 | 0 Months/RT | — | 1.00 | — | — | 0.10 | 0.30 | — | 0.20 | 0.10 | 0.05 | 0.85 | Fail for Yeast and Mold | Not Tested |
| Example | 0 Months/ | — | — | 0.26 | — | 0.10 | — | 0.30 | 0.26 | 0.10 | 0.05 | 1.53 | Failed | Not |

TABLE 1-continued

Preservative Agents and Test Results for an Oil-in-Water Emulsion

| Example No. | Storage Time & Temperature | Phospholipid CDM | Benzyl Alcohol | Chlorphenesin | Phenoxyethanol | Disodium EDTA | Sorbic Acid | Potassium Sorbate | Methylparaben | Propylparaben | Butylparaben | Water and/or Butylene Glycol | Micro Results Challenge | Micro Results Rechallenge |
|---|---|---|---|---|---|---|---|---|---|---|---|---|---|---|
| ple 9 | RT | | | | | | | | | | | | for Yeast and Mold | Tested |
| Example 10 | 0 Months/RT | — | 1.00 | — | — | 0.10 | — | 0.30 | 0.20 | 0.10 | 0.05 | 0.85 | Failed all organisms | Not Tested |
| Example 11 | 0 Months/RT | — | 1.00 | — | — | 0.10 | 0.20 | — | 0.20 | 0.10 | 0.05 | 0.95 | Failed for Mold | Not Tested |
| Example 12 | 0 Months/RT | — | — | — | 1.00 | 0.10 | — | — | 0.20 | 0.10 | 0.05 | 1.15 | Failed for organisms | Not Tested |

TABLE 2

Preservative Agents and Test Results for an Water-in-Oil Emulsion

| Example No. | Storage Time & Temperature | Phospholipid CDM | Benzyl Alcohol | Chlorphenesin | Phenoxyethanol | Disodium EDTA | Sorbic Acid | Potassium Sorbate | Methylparaben | Propylparaben | Butylparaben | Water and/or Butylene Glycol | Micro Results Challenge | Micro Results Rechallenge |
|---|---|---|---|---|---|---|---|---|---|---|---|---|---|---|
| Example 13 | 0 Months/RT | — | 1.00 | — | — | 0.10 | — | 0.40 | 0.20 | 0.10 | 0.05 | 0.55 | Passed | Passed |
| Example 14 | 1 Month/50° C. | — | 1.00 | — | — | 0.10 | — | 0.40 | 0.20 | 0.10 | 0.05 | 0.55 | Passed | Passed |
| Example 15 | 0 Months/RT | — | 1.00 | 0.15 | — | 0.10 | — | 0.40 | 0.25 | 0.10 | 0.05 | 0.35 | Passed | Passed |
| Example 16 | 1 Month/50° C. | — | 1.00 | 0.15 | — | 0.10 | — | 0.40 | 0.25 | 0.10 | 0.05 | 0.35 | Passed | Passed |
| Example 17 | 0 Months/RT | — | 1.50 | — | — | 0.10 | — | 0.40 | 0.20 | 0.10 | 0.05 | 0.05 | Passed | Passed |
| Example 18 | 0 Months/RT | — | — | 0.26 | — | 0.10 | — | 0.40 | 0.46 | 0.10 | 0.05 | 1.03 | Failed all organisms | Not Tested |
| Example 19 | 0 Months/RT | — | 1.00 | — | — | 0.10 | — | 0.40 | 0.20 | 0.10 | 0.05 | 0.55 | Failed for Yeast | Not Tested |
| Example 20 | 0 Months/RT | — | 1.00 | — | — | — | — | 0.30 | 0.20 | 0.10 | 0.05 | 0.75 | Failed for Yeast | Not Tested |
| Example 21 | 0 Months/RT | — | — | — | 1.00 | 0.10 | — | — | 0.20 | 0.10 | 0.05 | 0.95 | Failed all organisms | Not Tested |

TABLE 3

Preservative Agents and Test Results for an Water-Based Liquid

| Example No. | Storage Time & Temperature | Phospholipid CDM | Benzyl Alcohol | Chlorphenesin | Phenoxyethanol | Disodium EDTA | Potassium Sorbate | Sodium Benzoate | Methylparaben | Propylparaben | Butylparaben | Water and/or Butylene Glycol | Micro Results Challenge | Micro Results Rechallenge |
|---|---|---|---|---|---|---|---|---|---|---|---|---|---|---|
| Example 22 | 0 Months/RT | 0.50 | 1.00 | — | — | 0.10 | — | 0.50 | — | — | — | 0.40 | Passed | Passed |
| Example 23 | 1 Month/50° C. | 0.50 | 1.00 | — | — | 0.10 | — | 0.50 | — | — | — | 0.40 | Passed | Passed |
| Example 24 | 0 Months/RT | 0.50 | 0.95 | — | — | 0.10 | — | 0.40 | — | — | — | 0.55 | Passed | Passed |
| Example 25 | 1 Month/50° C. | 0.50 | 0.95 | — | — | 0.10 | — | 0.40 | — | — | — | 0.55 | Passed | Passed |
| Example 26 | 0 Months/RT | 0.50 | 0.50 | — | 0.50 | 0.10 | — | 0.40 | — | — | — | 0.50 | Passed | Passed |
| Example 27 | 1 Month/50° C. | 0.50 | 0.50 | — | 0.50 | 0.10 | — | 0.40 | — | — | — | 0.50 | Passed | Passed |
| Example 28 | 0 Months/RT | — | — | 0.15 | 1.00 | 0.10 | 0.40 | — | 0.15 | — | — | 0.70 | Passed | Passed |
| Example 29 | 0 Months/RT | — | — | 0.15 | 1.00 | 0.10 | — | 1.00 | 0.15 | — | — | 0.10 | Passed | Passed |
| Example 30 | 0 Months/RT | — | 1.00 | — | 1.00 | 0.10 | — | — | — | — | — | 0.40 | Passed | Passed |
| Example 31 | 0 Months/RT | — | — | 0.15 | 1.00 | 0.10 | — | — | 0.15 | — | — | 1.10 | Passed | Passed |
| Example 32 | 0 Months/RT | — | — | — | 1.00 | 0.02 | — | — | — | — | — | 1.48 | Failed for Mold | Not Tested |

TABLE 4

Preservative Agents and Test Results for a Water-Based Liquid Containing a High Level of Surfactants

| Example No. | Storage Time & Temperature | Phospholipid CDM | Benzyl Alcohol | Chlorphenesin | Phenoxyethanol | Disodium EDTA | Sorbic Acid | Potassium Sorbate | Methylparaben | Propylparaben | Butylparaben | Water and/or Butylene Glycol | Micro Results Challenge | Micro Results Rechallenge |
|---|---|---|---|---|---|---|---|---|---|---|---|---|---|---|
| Example 33 | 0 Months/RT | 0.50 | 1.00 | — | — | 0.10 | 0.40 | — | 0.20 | 0.10 | 0.05 | 0.05 | Passed | Passed |
| Example 34 | 1 Month/50° C. | 0.50 | 1.00 | — | — | 0.10 | 0.40 | — | 0.20 | 0.10 | 0.05 | 0.05 | Passed | Passed |
| Example 35 | 0 Months/RT | 0.50 | 0.95 | — | — | 0.10 | — | 0.40 | 0.20 | 0.10 | 0.05 | 0.10 | Passed | Passed |
| Example 36 | 1 Month/50° C. | 0.50 | 0.95 | — | — | 0.10 | — | 0.40 | 0.20 | 0.10 | 0.05 | 0.10 | Passed | Passed |
| Example 37 | 0 Months/RT | 0.50 | — | — | 1.00 | 0.10 | 0.30 | — | 0.20 | 0.10 | 0.05 | 0.15 | Passed | Passed |
| Example 38 | 1 Month/50° C. | 0.50 | — | — | 1.00 | 0.10 | 0.30 | — | 0.20 | 0.10 | 0.05 | 0.15 | Passed | Passed |
| Example 39 | 0 Months/RT | 0.50 | 1.00 | — | — | 0.10 | 0.30 | — | 0.20 | 0.10 | 0.05 | 0.15 | Passed | Passed |
| Example 40 | 1 Month/50° C. | 0.50 | 1.00 | — | — | 0.10 | 0.30 | — | 0.20 | 0.10 | 0.05 | 0.15 | Passed | Passed |
| Example 41 | 0 Months/RT | 0.50 | 0.50 | 0.04 | — | 0.10 | 0.30 | — | 0.14 | 0.10 | 0.05 | 0.67 | Failed all organisms | Not Tested |
| Example 42 | 0 Months/RT | — | 1.00 | 0.15 | — | 0.10 | 0.30 | — | 0.25 | 0.10 | 0.05 | 0.45 | Passed | Passed |
| Example 43 | 1 Month/50° C. | — | 1.00 | 0.15 | — | 0.10 | 0.30 | — | 0.25 | 0.10 | 0.05 | 0.45 | Passed | Passed |

TABLE 5

Preservative Agents and Test Results for a Water-Based Liposomal Preparation

| Example No. | Storage Time & Temperature | Phospholipid CDM | Benzyl Alcohol | Chlorphenesin | Phenoxyethanol | Disodium EDTA | Potassium Sorbate | Sodium Benzoate | Methylparaben | Propylparaben | Butylparaben | Water and/or Butylene Glycol | Micro Results Challenge | Micro Results Rechallenge |
|---|---|---|---|---|---|---|---|---|---|---|---|---|---|---|
| Example 44 | 0 Months/RT | — | 1.00 | — | — | 0.10 | — | 0.40 | 0.20 | 0.10 | 0.05 | 0.55 | Passed | Passed |
| Example 45 | 1 Month/50° C. | — | 1.00 | — | — | 0.10 | — | 0.40 | 0.20 | 0.10 | 0.05 | 0.55 | Passed | Passed |
| Example 46 | 0 Months/RT | 0.50 | 1.00 | — | — | 0.10 | — | — | 0.20 | 0.10 | 0.05 | 0.45 | Passed | Passed |
| Example 47 | 1 Month/50° C. | 0.50 | 1.00 | — | — | 0.10 | — | — | 0.20 | 0.10 | 0.05 | 0.45 | Passed | Passed |
| Example 48 | 0 Months/RT | 0.50 | — | — | 1.00 | 0.10 | — | — | 0.20 | 0.10 | 0.05 | 0.45 | Passed | Passed |
| Example 49 | 1 Month/50° C. | 0.50 | — | — | 1.00 | 0.10 | — | — | 0.20 | 0.10 | 0.05 | 0.45 | Passed | Passed |
| Example 50 | 0 Months/RT | 0.50 | — | 0.04 | 1.00 | 0.10 | 0.40 | — | 0.14 | 0.10 | 0.05 | 0.07 | Passed | Failed for Mold |
| Example 51 | 0 Months/RT | — | — | 0.15 | 1.00 | 0.10 | 0.40 | — | 0.25 | 0.10 | 0.05 | 0.35 | Passed | Passed |
| Example 52 | 0 Months/RT | — | — | 0.26 | 1.00 | 0.10 | 0.40 | — | 0.46 | 0.10 | 0.05 | 0.03 | Passed | Passed |
| Example 53 | 1 Month/50° C. | — | — | 0.26 | 1.00 | 0.10 | 0.40 | — | 0.46 | 0.10 | 0.05 | 0.03 | Passed | Passed |

TABLE 6

Specific Formulations of Ingredients for Examples 2–53

| | Examples 2–12 | Examples 13–21 | Examples 22–32 | Examples 33–43 | Examples 44–53 |
|---|---|---|---|---|---|
| Water | 51.886 | 63.69460 | 93.6136 | 52.4936 | 66.9946 |
| Magnesium Ascorbyl Phosphate | 3.000 | 0.0040 | 0.0040 | — | — |
| Grape Seed Extract | 0.005 | 0.0005 | 0.0005 | 0.0005 | — |
| Glycerin | 5.000 | — | — | 4.0000 | 4.0000 |
| Sorbitol (70% Solution) | — | — | — | 1.0000 | — |
| Butylene Glycol | — | — | — | — | 4.0000 |
| PEG-75 | — | — | — | — | 1.0000 |
| Xanthan Gum | 0.200 | — | — | — | 0.3000 |
| Carbomer | — | — | — | 0.0500 | 0.3000 |
| Acrylates/C10–30 Alkyl Acrylate Crosspolymer | — | — | — | 0.1500 | — |
| Glyceryl Polymethacrylate | 2.000 | — | — | — | 2.0000 |
| Disodium EDTA | 0.100 | 0.1000 | 0.1000 | 0.1000 | 0.1000 |
| Dipotassium Glycyrrhizinate | 0.100 | — | — | — | — |
| Sodium Chloride | — | 0.3000 | — | — | — |
| Methylparaben | 0.250 | 0.2000 | — | 0.2000 | 0.2000 |
| Stearamine Oxide | 2.500 | — | — | — | — |
| Polysorbate 20 | — | — | 2.0000 | — | — |
| Triethanolamine, 99% | — | — | — | 0.6500 | 0.4500 |
| Sorbic Acid | 0.400 | — | — | 0.4000 | — |
| Potassium Sorbate | — | 0.4000 | — | — | — |
| Sodium Benzoate | — | — | 0.4000 | — | 0.4000 |
| Dermasome TRF (Liposomal Preparation of Live Yeast Cell Derivative, Lecithin and Water from Brooks Industries) | — | — | — | — | 6.0000 |
| Dermasome P (Liposomal Preparation of Panthenol, Lecithin and Water from Brooks Industries) | — | — | — | — | 3.0000 |
| Witch Hazel Distillate | — | — | 2.0000 | — | — |
| Octyl Methoxycinnamate | 6.000 | 7.0000 | — | — | — |
| Benzophenone-3 | 3.000 | 2.0000 | — | — | — |
| Octyl Salicylate | — | 3.0000 | — | — | — |
| Octyl Palmitate | — | 6.0000 | — | — | — |
| Cetearyl Octanoate | 3.000 | — | — | — | — |
| C12–15 Alkyl Benzoate | — | 6.2500 | — | — | — |
| Isocetyl Stearate | — | — | — | 1.5000 | — |
| Tridecyl Stearate, Tridecyl Trimellitate, Dipentaerythrilyl Hexacapylate/Hexacaprate (Lipovol MOS-130, Lipo Chemical) | — | — | — | 24.0000 | — |
| Caprytic./Capric Triglyceride | — | — | — | 4.5000 | — |

TABLE 6-continued

Specific Formulations of Ingredients for Examples 2–53

| | Examples 2–12 | Examples 13–21 | Examples 22–32 | Examples 33–43 | Examples 44–53 |
|---|---|---|---|---|---|
| Glyceryl Stearate and PEG-100 Stearate (Lexemul 561, Inotex) | 3.500 | — | — | — | — |
| Glyceryl Stearate | — | — | — | 4.7500 | — |
| Polyglyceryl-4 Isostearate, Cetyl Dimethicone Copolyol and Hexyl Laurate (Abit WE09, Goldschmidt) | — | 5.0000 | — | — | — |
| Ceteareth-20 | — | — | — | 2.7000 | — |
| Cetyl Dimethicone | — | 1.0000 | — | — | — |
| Cyclomethicone (345 Fluid, Dow Corning) | 3.000 | 1.0000 | — | — | — |
| Dimethicone 350 cst | 1.500 | — | — | — | — |
| Phenyl Trimethicone | — | 0.5000 | — | — | — |
| Cetyl Alcohol | 0.900 | — | — | 0.5000 | — |
| Stearyl Alcohol | 0.900 | — | — | 0.5000 | — |
| Microcrystalline Wax | — | 1.2000 | — | — | — |
| Hydrogenated Castor Oil | — | 0.8000 | — | — | — |
| Phospholpid CDM | 0.500 | — | 0.5000 | 0.5000 | — |
| Propylparaben | 0.200 | 0.1000 | 0.1000 | 0.1000 | 0.0500 |
| Butylparaben | 0.050 | 0.0500 | 0.0500 | 0.0500 | 0.0100 |
| Octyl Palmitate, Titanium Dioxide, Alumina, Polyhydroxystearic Acid and Silica (Tioviel OP, Tioxide) | 3.670 | — | — | — | — |
| Zinc Oxide, Octyl Palmitate and Polyhydroxstearic Acid (Spectraviel OP, Tioxide) | 0.330 | — | — | — | — |
| Tocopheryl Acetate | 1.000 | 0.1000 | 0.1000 | 0.5000 | — |
| Retinyl Palmitate | 0.005 | 0.0005 | 0.0005 | 0.0005 | — |
| Ascorbyl Palmitate | — | — | — | 0.0050 | — |
| Benzyl Alcohol | 1.000 | 1.0000 | 0.9500 | 0.9500 | 1.0000 |
| Beta Glucan | 1.000 | 0.1000 | 0.1000 | 0.1000 | — |
| Panthonol and Water (50% Liquid, Roche Chemicals) | 2.000 | 0.2000 | 0.2000 | 0.2000 | — |
| Fagus Sylvatica Extract (Gatuline RC) | 2.000 | | | | |
| Saxifraga Stolonifera Extract, Grape Extract, Mulberry Root Extract, Scutellaria Root Extract, Butylene Glycol and Disodium EDTA (Phytoctar II) | 1.000 | — | — | — | — |
| Menthol | — | — | 0.0050 | — | — |
| Phytic Acid | — | — | 0.0010 | — | — |
| Bisabolol | — | — | 0.0100 | — | — |
| Superoxide Dismutase | 0.004 | 0.0004 | 0.0004 | 0.0004 | — |
| Fragrance | — | — | 0.0150 | 0.1000 | — |
| Total | 100.000 | 100.0000 | 100.0000 | 100.0000 | 100.0000 |

In view of the many possible embodiments to which the principles of our invention may be applied, it should be recognized that the illustrated embodiments are only some examples of the invention and should not be taken as a limitation on the scope of the invention. Rather, the scope of the invention is defined by the following claims, and equivalents thereto. We therefore claim as our invention all that comes within the scope and spirit of these claims, and equivalents thereof.

We claim:

1. A composition comprising one or more preservatives selected from the group consisting of a benzyl alcohol, an ethylene diamine tetracetic acid (EDTA), a para-hydrobenzoic acid, a salt of the para-hydrobenzoic acid, and an ester of the parahydrobenzoic acid, in an effective antimicrobial amount, combined with one or more enhancers selected from the group consisting of a sorbic acid, a salt of the sorbic acid, a benzoic acid, a salt of the benzoic acid, and a phospholipid, in an amount sufficient to increase an antimicrobial activity of the preservative.

2. The composition of claim 1, wherein the preservative comprises the benzyl alcohol in a concentration of about 0.5 to 3%.

3. The composition of claim 1, wherein the preservative comprises the benzyl alcohol in a concentration of about 0.75 to 2%.

4. The composition of claim 1, wherein the composition is a cosmetic, a skincare, a personal care or a pharmaceutical composition.

5. The composition of claim 4, wherein the composition is a pharmaceutical composition, and wherein the pharmaceutical composition is a dermatologic, an ophthalmic, or an otic formulation.

6. The composition of claim 1, wherein the enhancer is a phospholipid.

7. The composition of claim 6, wherein the phospholipid is present in the concentration range of about 0.5 to 1%.

8. The preservative system of claim 6, wherein the phospholipid is Phospholipid CDM, and wherein Phospholipid CDM is present in the concentration range of less than about 0.60%.

9. A topical composition, comprising:
one or more preservatives, wherein one of the preservatives is 0.5 to 3% of a benzyl alcohol or 0.05 to 0.15% of a disodium EDTA; and
one or more enhancers selected from the group consisting of a phospholipid, a sorbic acid, a potassium sorbate and a sodium benzoate, wherein each enhancer is present in a concentration of no more than about 1%, and wherein the combination of the enhancer with the preservative provides an effective antimicrobial effect.

10. The composition of claim 9, wherein the enhancer comprises at least 0.5% phospholipid.

11. The composition of claim 9, comprising one or more of a member of the group consisting of:
the phospholipid in a concentration of about 0.5%;
the sorbic acid in a concentration of about 0.3–0.4%;

the potassium sorbate in a concentration of about 0.3–0.4%; and the sodium benzoate in a concentration of about 0.4–1%.

12. A topical composition comprising:

a preservative comprising one or more of a benzyl alcohol and a salt of ethylene diamine tetracetic acid; and one or more enhancers selected from the group consisting of a phospholipid, a sorbic acid acids, a salt of sorbic acid, a benzoic acid, and a salt of a benzoic acid;

wherein the preservative and enhancer are present in an effective antimicrobial amount.

13. The composition of claim 12, wherein the enchancer comprises the phospholipid.

14. The composition of claim 12, wherein the preservative comprises both the benzyl alcohol and the salt of the ethylene diamine tetracetic acid.

15. The composition of claim 12, wherein the composition is an oil-in-water emulsion, a water-in-oil emulsion, a water based liquid, a water based liquid containing surfactants, or a liposomal suspension.

16. The composition of claim 12, wherein the composition is an aqueous composition containing a high concentration of surfactant, comprising about:

0.95–1% of the benzyl alcohol; and 0.5% of the phospholipid.

* * * * *

UNITED STATES PATENT AND TRADEMARK OFFICE
CERTIFICATE OF CORRECTION

PATENT NO.   : 6,120,758
DATED        : September 19, 2000
INVENTOR(S)  : Mukhtar Siddiqui, Ener H. Flores and Evasngeline R. Basa It is certified that error appears in the above-identified patent and that said Letters Patent is hereby corrected as shown below:

Title page,
Titled invention, "preservative system..." should read -- Improved Preservative System... -- as shown in the Request for Corrected Filing Receipt dated August 20, 1998.

Column 9,
Line 11, "Pa." should read -- PA --.

Column 17,
Line 26, "O" should read -- $O^-$ --.

Column 18,
Line 2, "$R_2$" should read -- $R_6$ --.
Line 16, "cargon" should read -- carbon --.
Line 29, "mount" should read -- amount --.

Signed and Sealed this

Sixth Day of November, 2001

Attest:

NICHOLAS P. GODICI
Attesting Officer   Acting Director of the United States Patent and Trademark Office